(12) United States Patent
Ellsworth et al.

(10) Patent No.: US 7,445,125 B2
(45) Date of Patent: Nov. 4, 2008

(54) METHOD AND APPARATUS FOR SEPARATING FLUID COMPONENTS

(75) Inventors: James R. Ellsworth, Marshfield, MA (US); Paul McGovern, Hanson, MA (US); Mark L. Kibbe, Carver, MA (US)

(73) Assignee: Harvest Technologies Corporation, Plymouth, MA (US)

( * ) Notice: Subject to any disclaimer, the term of this patent is extended or adjusted under 35 U.S.C. 154(b) by 258 days.

(21) Appl. No.: 10/538,323

(22) PCT Filed: May 19, 2004

(86) PCT No.: PCT/US2004/015654

§ 371 (c)(1),
(2), (4) Date: Jun. 10, 2005

(87) PCT Pub. No.: WO2004/104553

PCT Pub. Date: Dec. 2, 2004

(65) Prior Publication Data

US 2006/0151384 A1    Jul. 13, 2006

Related U.S. Application Data

(60) Provisional application No. 60/471,352, filed on May 19, 2003.

(51) Int. Cl.
*B04B 1/00* (2006.01)

(52) U.S. Cl. .......................... 210/518; 494/67; 422/101

(58) Field of Classification Search .................. 210/518; 422/101; 436/177
See application file for complete search history.

(56) References Cited

U.S. PATENT DOCUMENTS

| 280,820 | A | 7/1883 | Hickson |
|---|---|---|---|
| 593,333 | A | 11/1897 | Park |
| 3,409,165 | A | 11/1968 | Creith |
| 3,508,653 | A | 4/1970 | Coleman |
| 3,909,419 | A | 9/1975 | Ayres |
| 3,929,646 | A | 12/1975 | Adler |
| 3,931,010 | A | 1/1976 | Ayres et al. |
| 3,935,113 | A | 1/1976 | Ayres |
| 3,941,699 | A | 3/1976 | Ayres |
| 3,951,801 | A | 4/1976 | Ayres |
| 3,972,812 | A | 8/1976 | Gresl, Jr. |
| 4,001,122 | A | 1/1977 | Griffin |
| 4,088,582 | A | 5/1978 | Murty et al. |
| 4,152,270 | A | 5/1979 | Cornell |
| 4,364,832 | A | 12/1982 | Ballies |
| 4,417,981 | A | 11/1983 | Nugent |

(Continued)

FOREIGN PATENT DOCUMENTS

EP    1 106 252 A2    6/2001

*Primary Examiner*—Walter D. Griffin
*Assistant Examiner*—Cameron J Allen
(74) *Attorney, Agent, or Firm*—Clark & Brody

(57) ABSTRACT

A floating element for separating components of a physiological fluid comprises two parts that are relatively movable. The two parts define a prescribed volume between them when at their maximum separation, and one of the parts may be moved toward the other to express the fluid contained in the volume between the parts. The parts are made of materials having densities so that they assume a desired position in the fluid to allow selected components to be easily obtained are expressed.

23 Claims, 11 Drawing Sheets

U.S. PATENT DOCUMENTS

| | | |
|---|---|---|
| 4,818,386 A | 4/1989 | Burns |
| 4,844,818 A | 7/1989 | Smith |
| 4,853,137 A | 8/1989 | Ersson |
| 4,877,520 A | 10/1989 | Burns |
| 4,946,601 A | 8/1990 | Fiehler |
| 5,454,958 A | 10/1995 | Fiehler |
| 5,456,885 A * | 10/1995 | Coleman et al. ............ 422/101 |
| 5,533,518 A | 7/1996 | Vogler |
| 5,632,905 A | 5/1997 | Haynes |
| 5,707,876 A * | 1/1998 | Levine ....................... 436/177 |
| 5,736,033 A | 4/1998 | Coleman et al. |
| 5,860,937 A | 1/1999 | Cohen |
| 5,889,584 A | 3/1999 | Wardlaw |
| 5,918,622 A | 7/1999 | Perez |

* cited by examiner

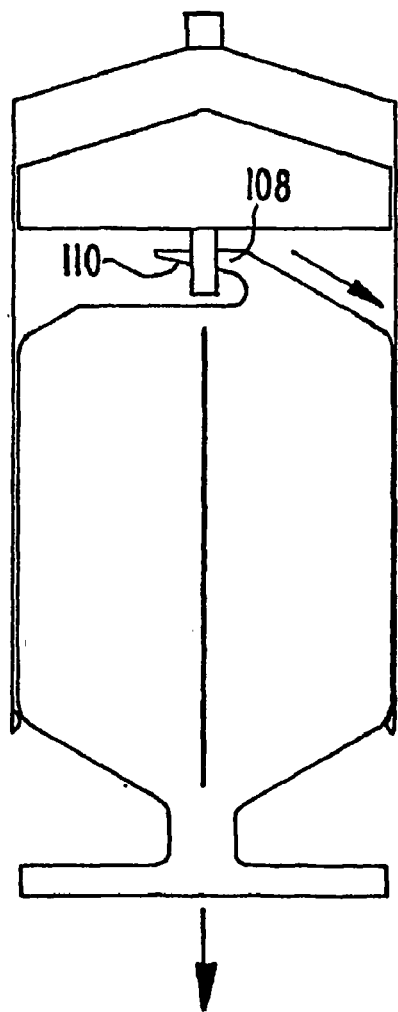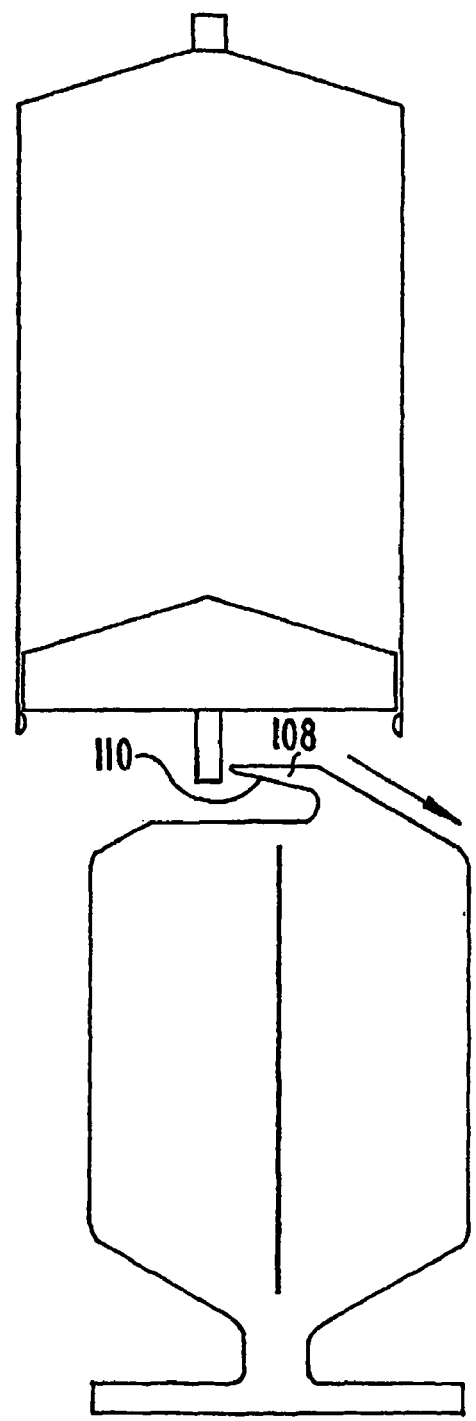

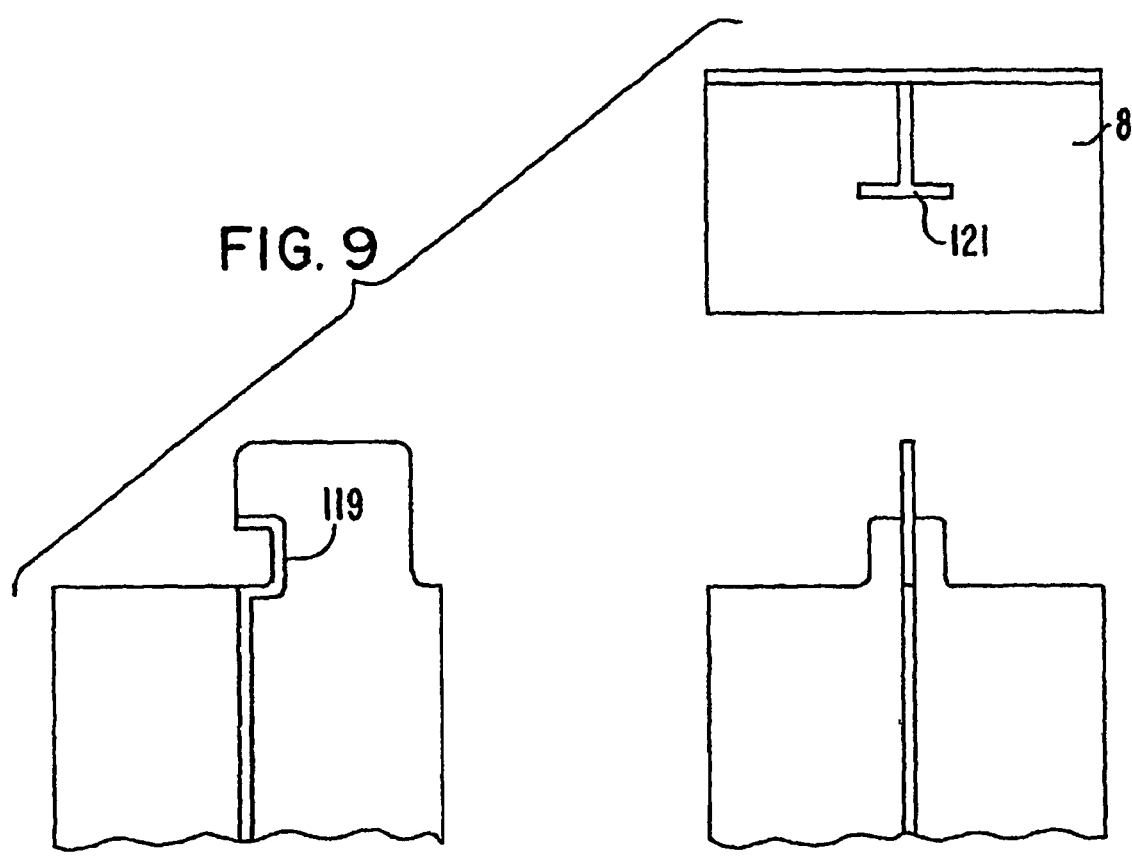

METHOD AND APPARATUS FOR SEPARATING FLUID COMPONENTS

This application is the national stage of International Application No. PCT/US2004/015654, filed May 19, 2004, which was published in English, and claims priority Of U.S. Provisional Application No. 60/471,352, filed May 19, 2003.

TECHNICAL FIELD

This invention relates to a unique element that floats in a physiological fluid undergoing centrifugation and assumes a location encompassing the boundary region between two components of different densities, and facilitates the isolation of a desired component found in the boundary region. Specifically, the floating element greatly facilitates the isolation and separation of the buffy coat from plasma and red blood cells.

Another aspect of the invention is the provision of a device for use both as a syringe for withdrawing physiological fluids and as a chamber for separating the components of the fluids. In its preferred embodiments, the invention is a syringe configured to withdraw fluids from a patient in known fashion and subsequently to be placed directly in the rotor of a centrifuge for separating components of different densities. The syringe is thereafter operated to express the components in serial fashion, for example, into separate cups.

BACKGROUND ART

Processing physiological fluids by centrifugation for separating the fluids into components of different densities is known. Physiological fluids include, for example, peripheral blood, umbilical cord blood, and bone marrow aspirate and ordinarily include cellular components. The physiological fluids subjected to the processes described herein may be obtained directly from a patient being treated, in which case the fluids are autologous, obtained from a donor, or obtained from a plurality of donors, in which case the fluids are homologous. While the objects of the invention are primarily concerned with the treatment of human fluids, it will be appreciated that the methods and apparatus described herein are equally applicable to fluids from other species.

A primary objective of the invention is to isolate and obtain a layer of cells that forms during centrifugation and includes, among other components, platelets, white cells, stem cells, and nucleated cells. This layer is known as the buffy coat, and its density is between that of the red blood cells (1.08-1.09) and that of plasma (1.017-1.026). Plasma with most of the cellular components removed is known as platelet poor plasma (PPP), while plasma with its cellular components is known as platelet rich plasma (PRP). Platelet rich plasma has been found to produce several beneficial effects, such as a more rapid healing of wounds. Thus, another objective of the invention is to provide plasma with an increased level of platelets. This is known as a platelet concentrate (PC) or more broadly as a cell concentrate (CC). A typical concentration is four or more times the native concentration, and a typical ratio of input volume to cell concentrate volume is 6:1. Platelet or cell concentrates obtained by the invention comprises the buffy coat and plasma and may include a small amount of red blood cells.

One of the problems addressed by the present invention is that the specific proportion of the various components and, even, the density of the cells themselves are unique to the particular donor, which precludes an exact a priori determination of the location of any given component in the fluid after centrifugation. For example, the proportion of red blood cells in blood, the hematocrit, varies with each patient, and the average density of the red blood cell component varies with its proportion of neocytes, young red blood cells, whose density is less than 1.08.

Furthermore, the particular technique used to collect the fluids impacts the density of the cells. An anticoagulant is typically added to blood as it is collected, and the amount of anticoagulant and the particular anticoagulant used affects the density, particularly, of red blood cells. This is termed the lesion of collection and results from the effect of the anticoagulant on the osmolarity of the cells. For example, when the anticoagulant is acid citrate dextrose, ACD, red cells become hypo-osmolar and the cells draw water through the dell membrane, which decreases the density of the cells. Other anticoagulants, such as tri-sodium citrate at a concentration of 3.8%, are somewhat hyper-osmolar, which results in shrinkage of the red blood cells and an increase in their density. CPD is iso-osmolar and has much less effect on the density of the cells. CPD and tri-sodium phosphate are preferred and have produced superior results in separations of the kind contemplated herein.

A further factor is that the layers of components form along the radius of centrifugation and are thus cylindrical, which complicates the design of structural elements for separating or collecting the layers.

A system for separating blood into components for producing a platelet concentrate is described in U.S. Pat. No. 6,398,972. The system described in that patent uses a disposable processing unit having two chambers. Blood is drawn into a known syringe and expressed from the syringe into a first chamber of the processing unit. The processing unit is then placed in a centrifuge designed to automatically transfer supernatant fluids from one chamber to another. After a first centrifugation, platelet rich plasma is transferred into the second chamber, and the centrifuge is operated a second time to separate platelets from platelet poor plasma. While this system has many advantages, it has the disadvantage that the blood must be transferred from the syringe to the processing unit, and the centrifuge and the orientation of the processing unit must be controlled to decant the platelet rich plasma to the second chamber.

The first chamber of the system described in the '972 patent includes a disk that is positioned generally at the intersection of the red blood cells and the plasma to prevent decanting of red blood cells into the second chamber.

U.S. Pat. No. 5,456,885 shows a system wherein a collection tube is placed directly in a centrifuge to allow separation of the components. A floating element assumes a position between the plasma and the red blood cells and also acts as a check valve when the lighter phase is expressed from the tube. Systems of this type are, however, not generally capable of separating the buffy coat from the platelet-poor plasma and the red blood cells.

The known centrifuges operate according to a particular protocol when it is desired to obtain a component of intermediate density. For example, when the object is to obtain platelets, it is known to subject blood to a first centrifugation to separate heavier components, such as red blood cells, from plasma, transferring the plasma to a second container or chamber by decanting and then subjecting the plasma to a second centrifugation to separate the plasma from the platelets. The platelets are then separated from the plasma in a second decanting step.

Known techniques for obtaining the desired component of intermediate density are complicated because they require multiple centrifugations and multiple decant or centrifugal transfer steps. Also, the separation of a single component is often complicated because the physical, fluid properties of the desired component may tend to cause it to mix with the other components.

The buffy coat layer is easily disrupted, and when one attempts to express platelet poor plasma through the tip of a syringe, the buffy coat often mixes with the plasma or with the red blood cells. This effectively prevents the expressing of the buffy coat layer either by itself or with only a negligible amount of the other components.

As well, known tubes or syringes designed to be supplied directly to a centrifuge are difficult to use effectively.

SUMMARY OF THE INVENTION

In accordance with the invention, an improved device is provided for separating components having differing densities in a centrifuge and isolating and dispensing a desired one of these components. The device may take the form of a syringe in the sense that it can be provided with a plunger and operated to draw a fluid, such as blood, bone marrow aspirate, or other physiological fluids, into a chamber through one end and to express the components through that end after separation. The device may, however, be a container of other configurations capable of being placed in a centrifuge and not necessarily designed to operate as a syringe.

A particular objective of the invention is to obtain a cell concentrate from whole blood (including umbilical cord blood), bone marrow aspirate, or other physiological fluid in an efficient fashion through centrifugation and the expressing of the several components. The cell concentrate preferably includes the buffy coat, some red cells, and plasma in desired ratio. The buffy coat is a thin layer that forms during centrifugation and includes mostly all of the cells other than the red blood cells. The buffy coat is known to include platelets, white cells, nucleated cells, and stem cells and may include other components as well. Because the buffy coat is a somewhat diffuse layer that is easily disrupted and mixed with the other components, which reduces the effectiveness of the procedure, an object of the invention is to provide a container that can be operated to dispense the cell concentrate without significant mixing of the desired cells with the plasma or the red blood cells. This is accomplished in the preferred embodiments primarily by providing a flow path for the cell concentrate that reduces mixing between the components. In the preferred embodiments, a disk assembly floats in a region containing an interface between plasma and the buffy coat and a diffuse interface between the buffy coat and the red cells, and assists in separating those components. As well, the disk assembly is shaped so that it forms a flow path for the components and reduces turbulence during separation of the components to prevent mixing the components during their expression.

In its preferred embodiment, a disk assembly that is allowed to float in the fluid presents a vertical gradient in the buoyant forces that cause it to assume a position in the region having the desired component, e.g., the buffy coat. This gradient is provided either by the shape of the assembly, by the use of materials of different densities, or by a combination of both. In the preferred embodiment, the disk assembly provides a conical upper surface, and an upper portion of the assembly is made of a material that is less dense than red blood cells but more dense that plasma. A lower portion of the assembly is made of a material that is denser than the red blood cells. Because of the conical shape, the buoyant force provided by the upper element at the boundary between the plasma and the red blood cells and in the region of the buffy coat is a non-linear function of the distance by which the upper element extends into the plasma. The density gradient of the fluids in the boundary region is large, and the use of a floating element with a density gradient also has been found to be beneficial.

The disk assembly according to the invention is designed to encompass both a desired component and a predetermined volume of fluid surrounding the desired component. In the preferred embodiment, the disk assembly comprises two floating parts that are movable relative to each other whereby the entire assembly is caused to assume a desired position after centrifugation, and one part moves toward the other during expression of the fluids to express a desired component or components, e.g., the buffy coat and a predetermined volume of plasma. This structure allows the user to obtain a cell concentrate comprising the buffy coat mixed with plasma at a desired increased concentration.

The invention also relates to perfecting mechanical features, such as a handle for a plunger that accommodates placing the syringe in a centrifuge, and a stand for holding the syringe after centrifugation for facilitating expression of the components. The handle may be detachable or flexible whereby the distance by which it extends from the end of the barrel when the syringe is full is greatly reduced.

It is an object of this invention to provide a device for use in separating the various components of a fluid by placing the fluid in the device, subjecting the device and fluid to centrifugation, and then expressing the components.

It is a further object of this invention to provide a syringe for withdrawing fluids from a container or from the patient, for being placed directly into a centrifuge, and for expressing the separated components in serial fashion with minimal mixing.

BRIEF DESCRIPTION OF THE DRAWINGS

FIGS. 7a and 7b are side views of a syringe according to the invention showing a second embodiment of plunger handles that can be detached.

FIG. 9 shows yet another embodiment of a detachable handle.

DETAILED DESCRIPTION OF THE PREFERRED EMBODIMENTS

The invention will be described below in accordance with its operation as a syringe. Use with a syringe is advantageous because it allows the user to withdraw the physiological fluid into the syringe, place the syringe directly into a centrifuge for centrifugal processing, and then to express the several components from the syringe into separate containers. As such, this procedure requires only a single container without intermediate decanting steps. It will be understood, however, that many features of the invention do not require operation with a syringe or a single container and that the disk assembly to be described below may be used in combination with other containers as well.

A floating element that automatically assumes a position just below the buffy coat is disclosed in WO 01/83068. The disk disclosed there is useful to separate the components of physiological fluids by centrifugation and finds its primary utility in structures that separate the components after centrifugation by decanting. The disk shown there is useful, however, to separate components when used with a structure such as a syringe, and several examples of such use are described in U.S. Provisional Patent Application 60/471,352, the disclosure of which is hereby incorporated by reference.

Figure 1:
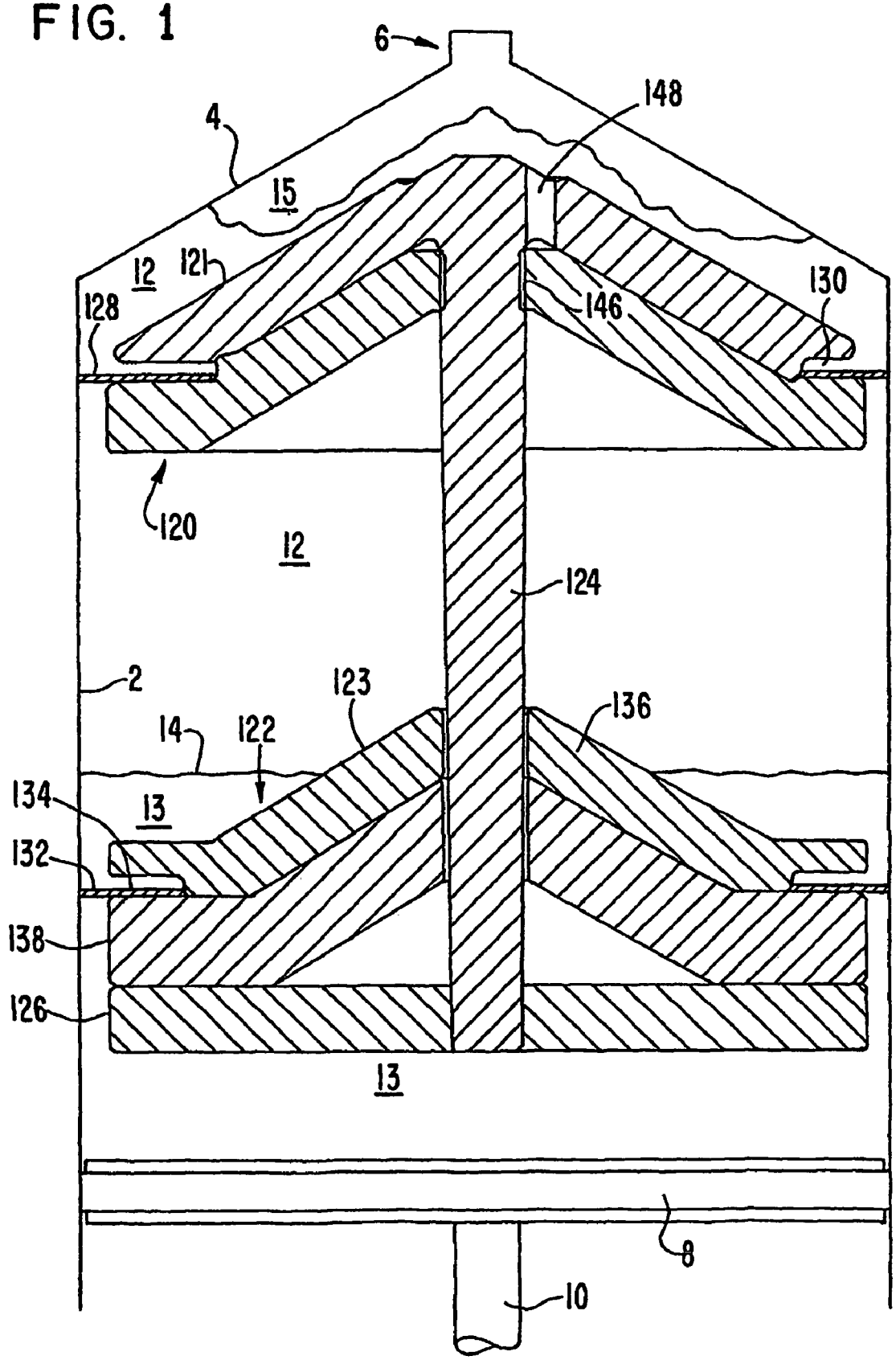
FIG. 1 is a vertical cross section of a first embodiment of a syringe according to the invention.

A primary objective of the present invention is to facilitate the production of a cell concentrate having a defined volume of plasma and at least a major portion of the buffy coat. With reference to the drawings, FIG. 1 shows a preferred embodiment of a disk assembly in combination with a known syringe, which includes a cylindrical barrel portion 2, a conical end portion 4, and a tip portion 6. The syringe also includes a piston or plunger 8, which fits tightly in the cylindrical barrel and moves longitudinally to draw fluids into the barrel or express fluids from the barrel. A handle 10 is attached to the plunger and is typically configured so that an operator can easily grasp it to move the plunger within the barrel. This structure is commonly found on syringes that can be obtained from many sources.

In accordance with the embodiment shown in FIG. 1, a disk assembly comprises an upper element 120 and a lower element 122 that is slidingly mounted on a pin 124 for relative movement with respect to element 120. A third element 126 primarily provides lateral stability to the disk assembly and is mounted on the pin 124 in a fixed position. Thus, in the embodiment of FIG. 1, the three elements float in the fluid and assume a predetermined position s will be described below. It will be appreciated that since element 122 is movable along the pin that some lateral stability can be lost when the distance between the upper element 120 and the movable element 122 is small and that the presence of the washer element 126 maintains stability. Other means for providing such stability such as longitudinally extending skirts may be used as well.

It will also be appreciated that the presence of the washer 126 determines the maximum distance by which the element 122 can be displaced downward from the upper element. That maximum distance may be determined by other means, such as by a stop on the pin 124.

In the preferred embodiment, the disk assembly comprising elements 120, 122, and 126 is made of materials selected and configured such that the washer 126 assumes a position near the top of the layer of red blood cells. Preferably, the assembly is designed so that the "buffy coat," lies just on the upper surface of the movable element 122, possibly with a few red blood cells also. This arrangement works particularly well when the objective is to separate platelets, stem cells, white cells, and other cells from the red blood cells and plasma. The primary use of the preferred embodiments of the invention is to separate, red blood cells, plasma, and the mix of cells typically found in the buffy coat from whole blood, bone marrow, bone marrow aspirate, or umbilical cord blood, and the embodiments of this invention will be described below in that context. It should be noted, however, that the methods and devices of the invention could be used to separate other fluids into components having different densities.

The operator first draws blood into the syringe by pulling the piston away from the conical end. The tip of the syringe may be connected to any one of several types of sources, and in the preferred embodiment, the syringe is attached to a needle so that blood is drawn into the syringe directly from a patient. The blood may be drawn from other places, such as a bag of blood obtained from the patient. The syringe having blood therein is then placed in a centrifuge and subjected to centrifugation to cause the components of differing densities to separate into layers along the barrel. While the preferred structure by which the syringe is placed in the centrifuge will be described in detail below, it will be appreciated that a variety of structures may be used to attach the syringe to the rotor of a centrifuge.

In accordance with a preferred embodiment, during centrifugation the disk assembly eventually assumes a position between red blood cells and platelet poor plasma, where the buffy coat 14 lies on the upper surface 123 of the element 122. When the centrifugation is stopped, platelet poor plasma 12 will be the upper layer (up being the orientation with the tip of the syringe pointing upward), red blood cells 13 will be the bottom layer, and the buffy coat 14 will be the intermediate layer. It will be understood that the layers as illustrated in FIG. 1 are not exact, particularly because the boundary between red blood cells and the buffy coat is diffuse.

It will also be appreciated that the distance between the upper element 120 and the movable element 122 determines volume of plasma 12 captured between these elements. Thus, after centrifugation, plasma will surround the upper element 120, and red blood cells will surround the washer 126 and extend onto a small part of the upper surface of the movable element 122. After centrifugation, the user pushes on the handle 10 to expresses the components in serial fashion.

The buffy coat is quite thin, and a common problem faced when expressing the components is that turbulence occurring during expression, which causes the buffy coat to mix with the plasma and red blood cell layers. Thus significantly reduces the ability to express the buffy coat as a separate component or layer. In accordance with a primary aspect of the invention, the internal structure of the syringe is designed to provide a pathway for the fluids being expressed that avoids mixing the components. Because the buffy coat lies on the upper surface of the disk in the preferred embodiments, the configuration of the disk is preferably designed to cooperate with the internal surfaces of the syringe to provide the desired pathway.

The top surface 121 of the upper element 120 is preferably conical to conform to the shape of the conical end 4 of a syringe, whereby it will engage the end of the syringe during expression of the fluids. Other shapes are, of course possible. The upper element 120 includes a flexible seal 128, which is preferably a thin annulus made of plastic that is flexible enough to allow cells to pass it during centrifugation but to resist that in normal handling of the syringe. In the preferred embodiment shown in FIG. 1, the upper element is made of two parts, and the seal rides freely in groove 130 formed between the two parts. The movable element 122 is also made of two parts and includes a seal 132 that rides in groove 134.

The flexible seals 128 and 132 reduce mixing of the components during expression and handling, when the syringe may be placed in different orientations, e.g., when the user lays it horizontally on a table. Thus, the seals prevent flow of the red blood cells from below the seal 132 into the predefined area between the upper and movable elements, which would reduce the effectiveness of the separation of the components. The provision of the seals also increases the allowable manufacturing tolerances and greatly reduces the possibility that deformations in the syringe barrel during operation of the syringe will adversely affect the operation of the device.

Element 122 includes several features that allow it to assist in positioning the disk assembly itself such that a small layer of red blood cells 13 lies just above the upper surface 123 of the element 122 and below the buffy coat 14. This ensures that the entire buffy coat is obtained and facilitates the expression of the buffy coat because the red blood cells tend to prevent attraction between the buffy coat and the upper surface of the movable element. Also, because the boundary between the buffy coat and the red blood cells is diffuse, it is not generally possible to obtain the entire buffy coat without including a small amount of the red blood cells.

The movable element 122 preferably includes a vertical density gradient provided by an upper part 136 having a density of about 1.04 and a lower part 138 having a density of approximately 1.08. By this construction, the two parts of the movable part both tend to sink in the plasma, the upper part, however, floats in the red blood cells, and the lower part sinks in red blood cells. In addition to the density gradient presented by the use of the two materials, it will be appreciated that the conical shape of the element 136 causes the gradient of the buoyant forces to be non-linear at the boundary between the plasma and red blood cells. This has been found to increase the ability of the floating element to position itself such that the buffy coat lies either on the conical surface 123 or just above it.

In operation, fluids are drawn into the syringe, and some air is also drawn in. After centrifugation, the air will form a bubble at the top of the syringe. If the syringe is then inverted to express the platelet poor plasma between the element 120 and the end of the syringe, the bubble will move to a position between element 120 and the plasma. At that point, the user may express the platelet poor plasma into a cup. The user will know that the platelet poor plasma has been expressed when the air bubble 15 reaches the tip of the syringe. At that point the user can express the air until the upper end of the element 120 contacts the conical end of the syringe. At that point, further movement of the plunger will cause the red blood cells below the element 122 to move element 122 upward to express the plasma and buffy coat that lie between the elements 120 and 122. These materials will flow through a channel 146 between the pin 124 and the lower part of element 120 and then through a hole 148 in the upper part. As the plunger is advanced, the element 122 will move upward until all of the material between elements 120 and 122, namely the plasma and the buffy coat, and a few red blood cells in the preferred embodiment, has been expressed. At this point, the force required to advance the plunger will increase significantly because the red blood cells will have to move past the seals 132 and 128. The user will notice this increase in force and will recognize it as indicating that all of the material has been expressed.

While the syringe is usually cylindrical, it may have other shapes. For example and oval cross section may be useful to prevent rotation of the parts.

Figure 2:
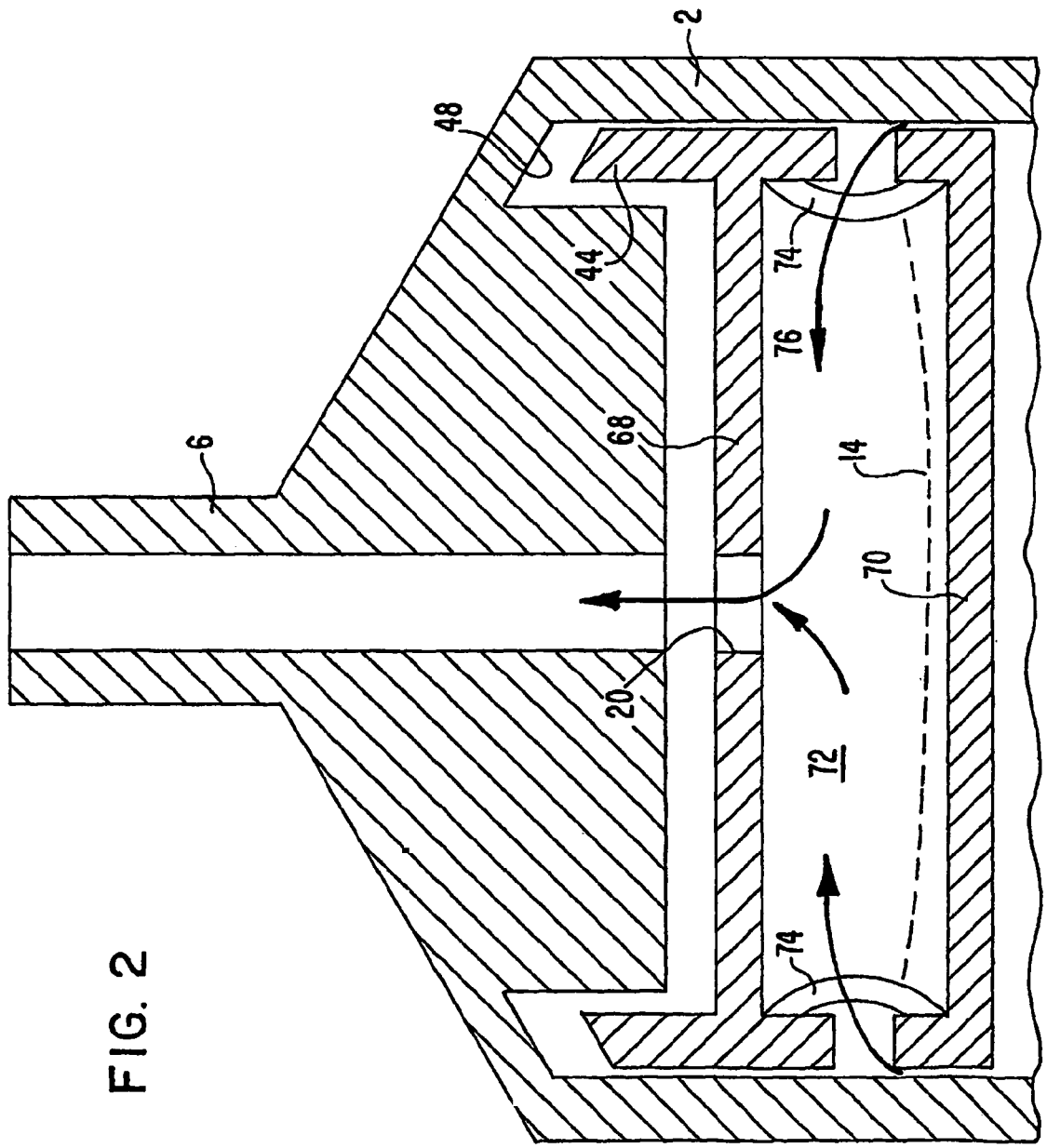
FIG. 2 is a vertical cross section of a second embodiment of a syringe according to the invention.

FIG. 2 illustrates an embodiment where the disk assembly comprises upper part 68 and lower part 70. The upper and lower disks form a cavity 72 between them, and the densities of the upper and lower parts are chosen such that the buffy coat 14 lies in the space 72. The upper and lower parts may be attached together by circumferentially spaced strips 74 that allow fluids passing between the periphery of the lower part 70 and the wall 2 of the barrel portion to flow into the cavity 72.

The embodiment of FIG. 2 is advantageous because it captures the buffy coat in the relatively small space 72 between the upper and lower parts 68 and 70. This space is preferably made to be sufficiently small that the buffy coat will not mix with the plasma even if the syringe is not maintained in a strictly upright orientation or if the syringe is otherwise tilted or moved about in a fashion that would cause mixing in the embodiments described earlier. It will be appreciated that it is generally necessary to maintain the syringe upright so that the components that are to be dispensed separately are not mixed with each other. Thus, the embodiment of FIG. 2 is aimed at reducing the requirement for handling the syringe with extreme care not to mix the components.

The buffy coat is expressed in the embodiment of FIG. 2 much the same as in the other embodiments. As the piston or plunger of the syringe is advanced, the plasma is expressed first until the skirt portion 44 engages the syringe, and the red blood cells then flow into the cavity 72 as shown at 76 and flush the buffy coat upward through opening 20 and through the tip 6. It will be appreciated that the upper part 68 of the disk shown in FIG. 2 includes a skirt 44 that engages in the annular portion 48. Also, the upper end of the syringe is flat, and the upper surface of the upper element 68 is also generally flat to reduce the volume between these two when the disk is in the uppermost position. It will be understood, however, that the upper surface of the disk 68 could be conical if the upper end of the syringe were conical.

Also, the upper surface of the disk can contact and seal against the inner surface of the syringe.

Figure 3A:
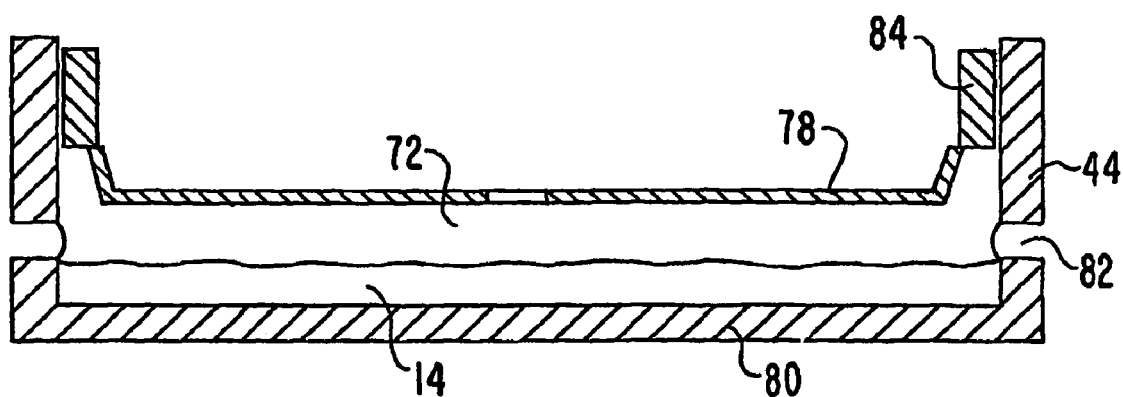
FIGS. 3a and 3b are vertical cross sections of a third embodiment of a syringe according to the invention.
Figure 3B:
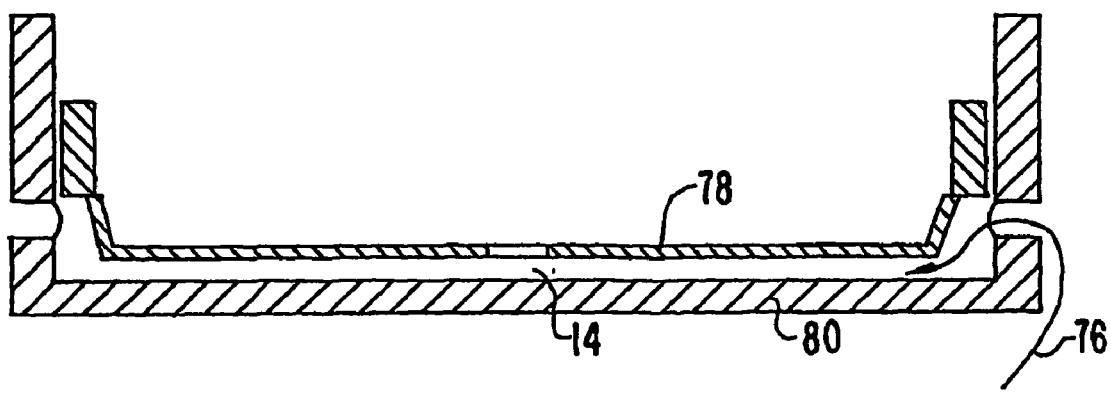

FIGS. 3a and 3b illustrate another embodiment that has a two-part disk. In this embodiment, the upper part 78 of the disk may move with respect to the lower part 80. Thus, the lower part 80 is provided with a skirt 44 and openings 82 to allow fluid to flow radially inward during expression of the buffy coat. The upper part 78 is made of material less dense than plasma (e.g., LDPE) and is supported on the skirt by elements 84 that allow vertical movement of the upper element along the skirt. Of course other arrangements may be provided to provide this motion. The result is that the buffy coat will be contained in the cavity 72 between the two elements. Because the upper element floats in the plasma, the space 72 will initially be larger than required to contain only the buffy coat. Both parts of the disk will move upward during expression of the plasma, and the upper part will eventually engage the end of the syringe. As the plunger is moved further upward, the lower part will move upward further as illustrated in FIG. 3b while the upper part is constrained against further movement. This will reduce the size of the space 72 and express the plasma and then the buffy coat from the syringe.

Figure 4A:
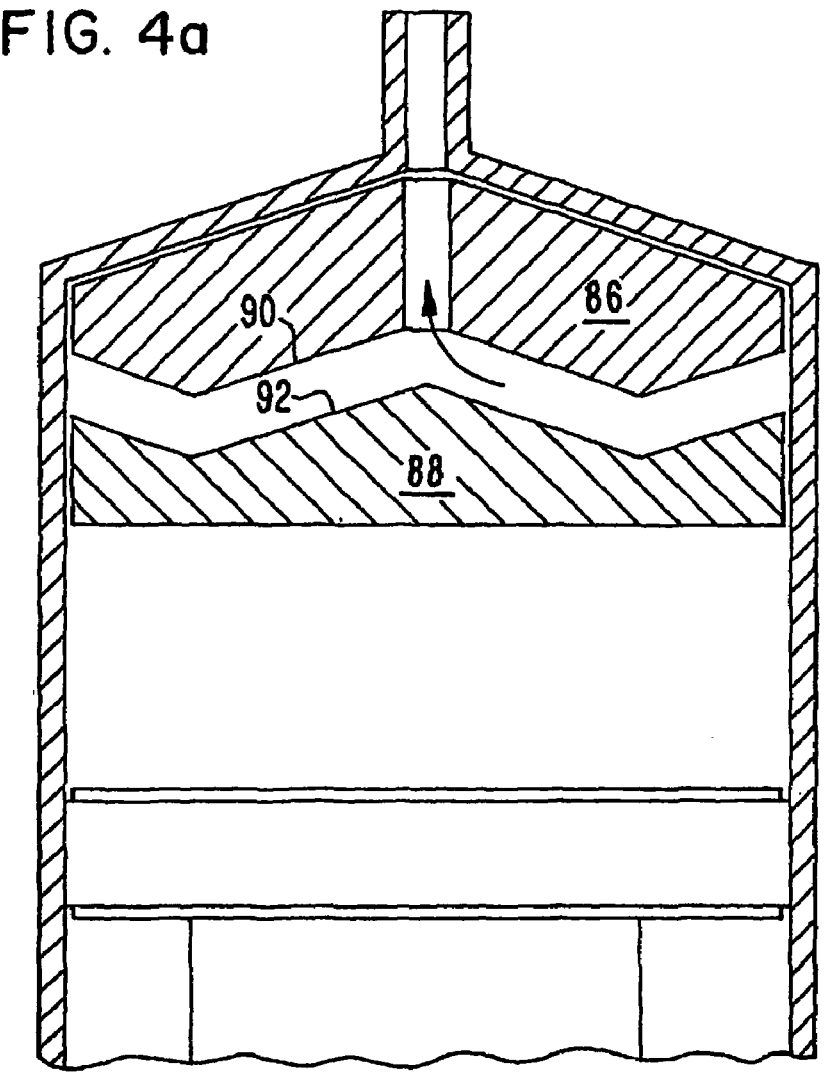
FIGS. 4a and 4b are vertical cross sections of a fourth embodiment of a syringe according to the invention.
Figure 4B:
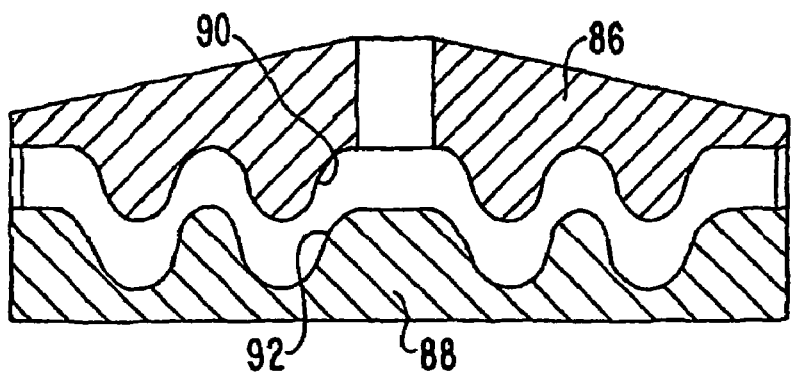

FIGS. 4a and 4b show yet another modification wherein an upper part 86 and a lower part 88 of the disk are configured to provide an annular trough for receiving the buffy coat. These two parts may be configured to move with respect to each other as in the embodiment of FIG. 3. In the embodiment of FIG. 4a the upper part 86 has a protruding annular portion 90, and the lower part has an annular trough 92 that matches the portion 90. The trough 92 receives the buffy coat, and when the fluids flow radially inward during expression the buffy coat is expressed as illustrated by the arrows.

FIG. 4b shows a similar concept where the surfaces 90 and 92 are serpentine.

Figure 5:
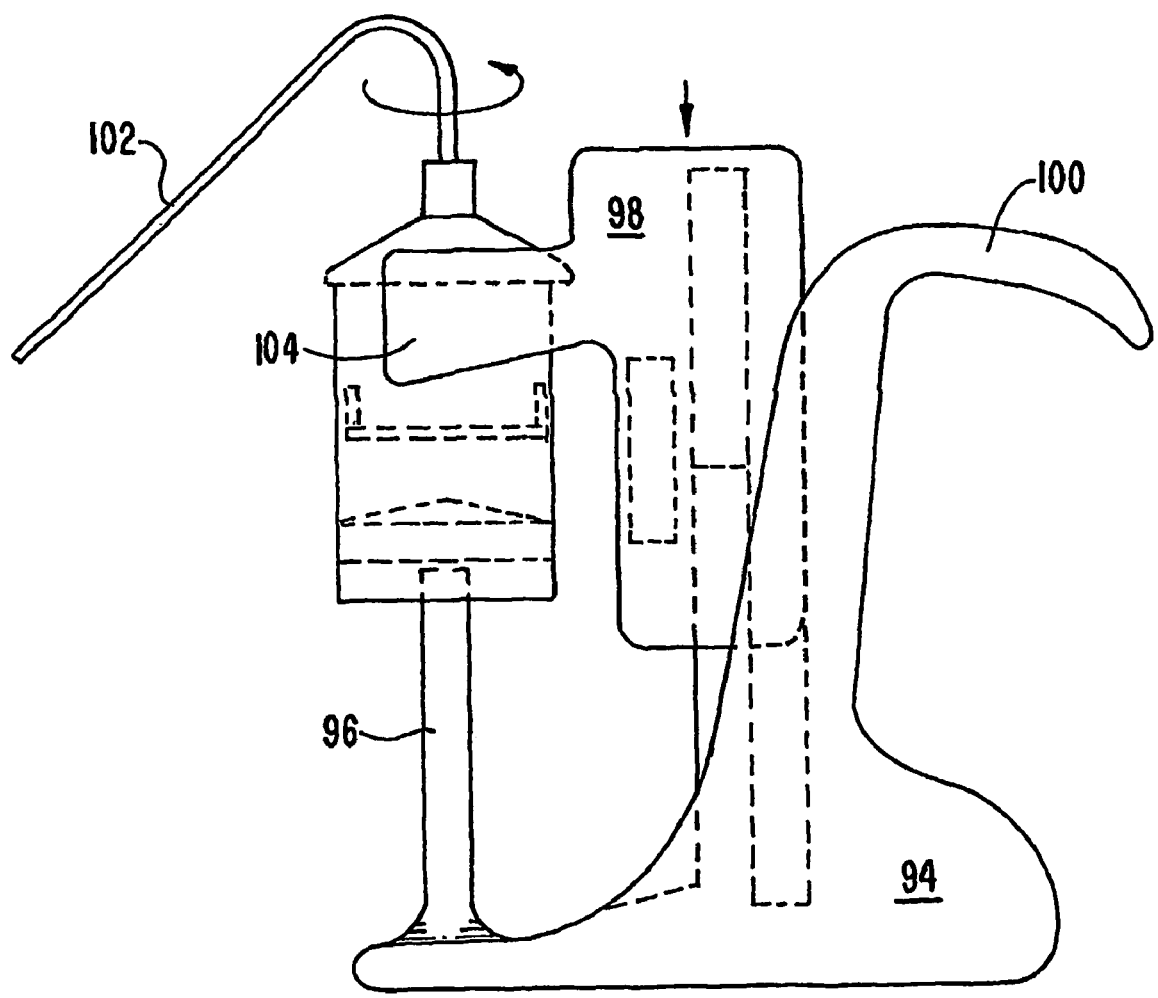
FIG. 5 is a side view of a stand, or holder for engaging a syringe of the invention.

The previous discussion has not assumed any particular mechanism for advancing the piston or plunger. FIG. 5 shows an optional stand designed to hold a syringe and facilitate expression of the components. The stand includes a base 94 that includes a vertical rod 96 on which the syringe is placed so that the rod contacts the piston or plunger. The syringe is engaged by a movable carriage 98, which is fitted to the base by coacting elements to ride vertically on the base. The user's fingers may grasp a handle 100, and the user's thumb can engage the top of the carriage 98. Thus, the user can push the syringe downward against the rod to move the piston upward and express the components. A tube 102 is connected to the tip of the syringe to direct the components to the desired container, such as small cups for receiving, for example, platelet poor plasma and the buffy coat. An optical element may be mounted on a projection 104 to provide audible or other signals regarding the boundaries of the components to be expressed.

Figure 6A:
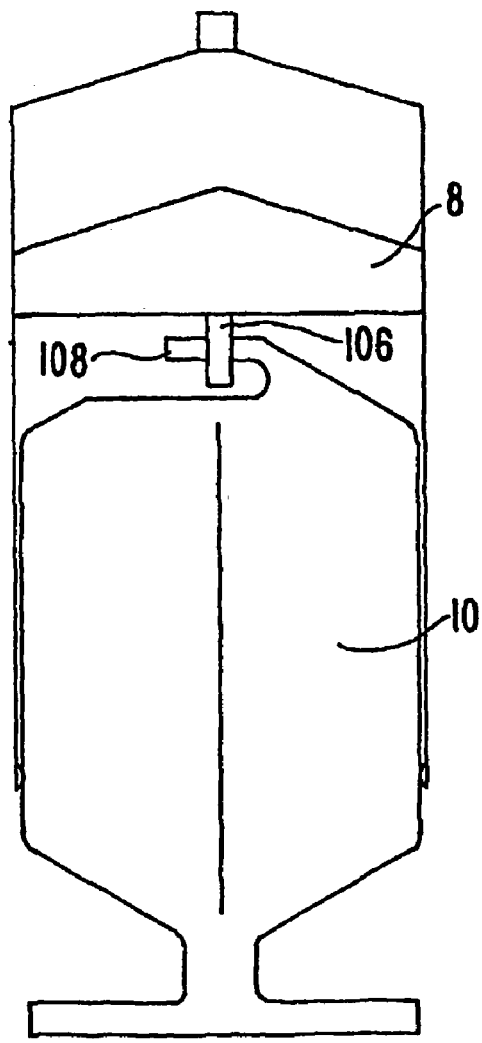
FIGS. 6a and 6b are side views of a syringe according to the invention showing a first embodiment of plunger handles that can be detached.
Figure 6B:
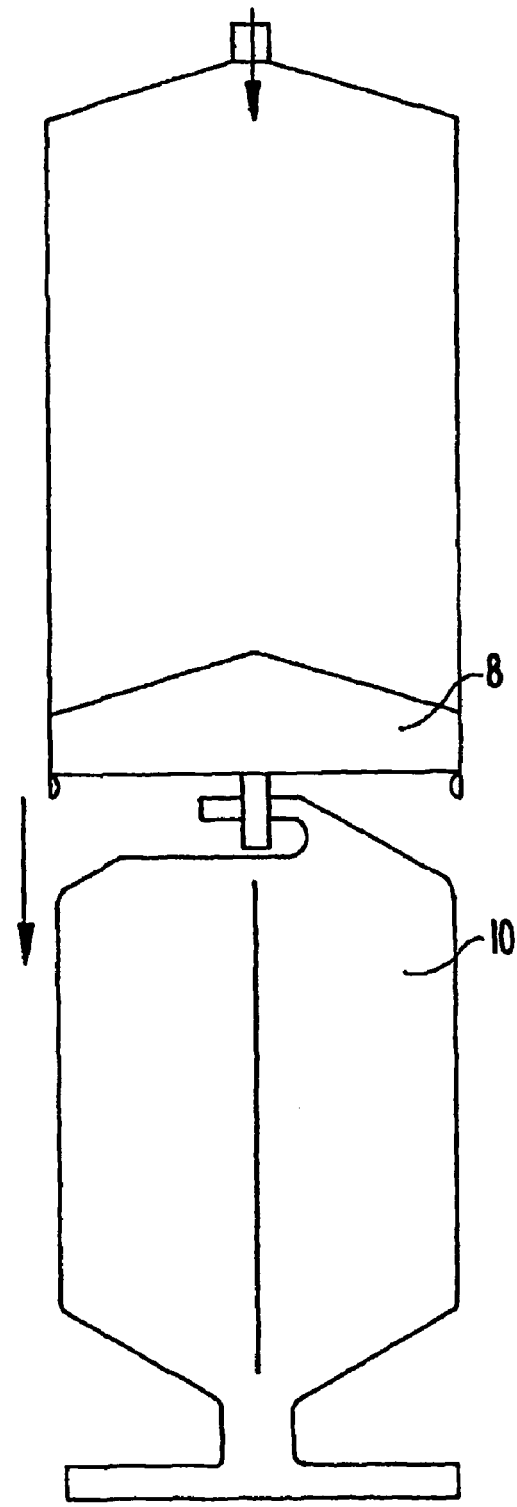

FIGS. 6 and 7 illustrate alternate designs for the syringe whereby the handles are easily removed. For example, the handles should be removed before the syringe is placed in a centrifuge. After centrifugation, the syringe may be placed in a stand such as that shown in FIG. 5, the handle reinstalled, or the like. As shown in FIG. 6a, the plunger 8 may include a tab 106 that engages a hook 108 or similar element on the end of the handle 10. The hook may be disengaged when the piston is fully withdrawn as shown in FIG. 6b. FIGS. 7a and 7b show a similar arrangement except that the lower surface 110 of the hook is angled whereby it automatically disengages. Thus, when the handle is not fully withdrawn, the side of the handle engages the barrel portion of the syringe and prevents disengagement. When the handle is fully withdrawn, the handle is then able to move transversely with respect to the barrel, and application of a longitudinal force to the handle, as is normal when withdrawing the piston, automatically applies a transverse force to the hook, causing it to disengage as shown in FIG. 6b.

Figure 8B:
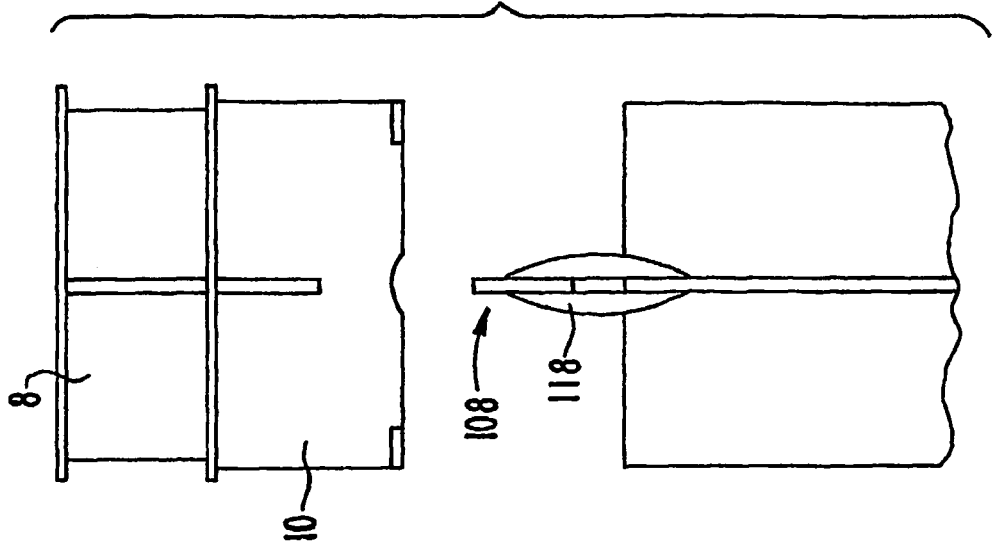
FIGS. 8a and 8b illustrate a further embodiment of a detachable plunger.
Figure 8A:
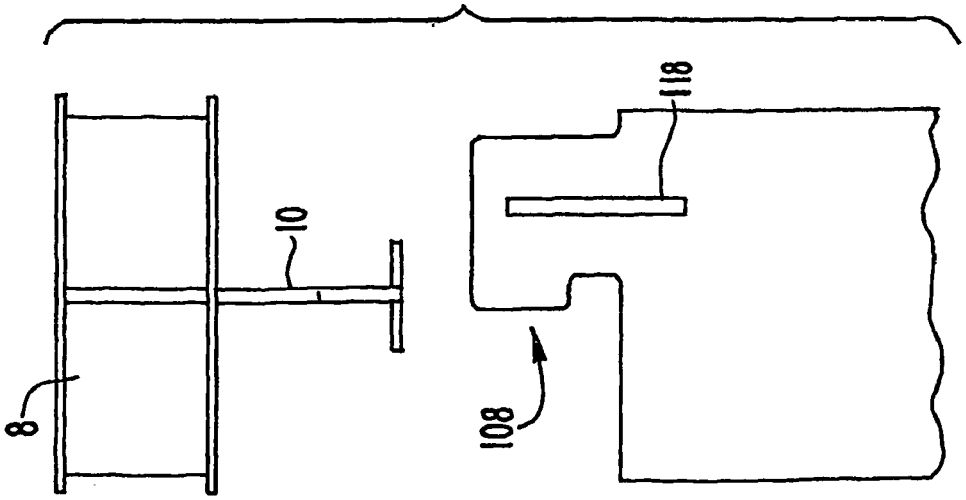

FIGS. 8a and 8b show additional details of the structure of the hook 108. The hook shown in these figures is reinforced by a flange 118, which stiffens it against bending.

FIG. 9 illustrates a hook that has a reinforcing rib 119 that is received in a slot 121 in the plunger Alternatively, the handle may be configured such that its shape can be changed such that the syringe may be placed in the centrifuge. As one example, the handle may be configured so that it can be bent to a position that allows the syringe to be placed in the centrifuge.

Figure 10A:
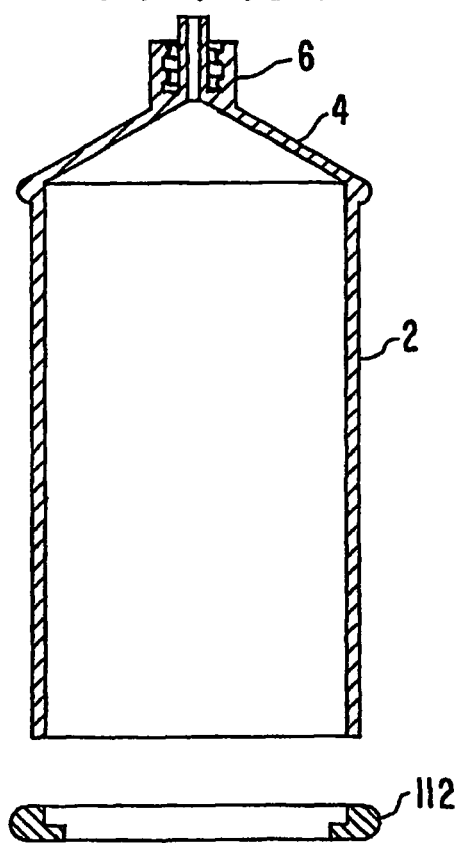
FIG. 10a illustrates a syringe having a ring that retains a piston.
Figure 10B:
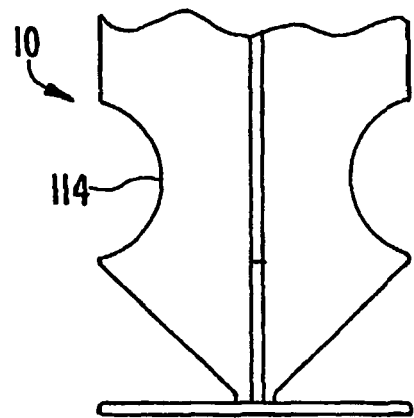
FIG. 10b illustrates a plunger handle that has been modified to accommodate the ring during assembly.

FIG. 10a illustrates structure that facilitates construction of a syringe according to the invention. To assemble the syringe, the disk assembly and the plunger 8 must be inserted into the barrel 2. A stop must be provided to prevent withdrawal of the plunger when the syringe has been filled with blood. Thus, as shown in FIG. 10a, a ring 112 is provided that is attached to the end of the barrel. Preferably, the ring 112 is spin-welded to the barrel during manufacture. FIG. 10b shows a handle 10 with a depression 114 that provides space for the spin-welding machinery to be attached to the ring 112 during manufacture.

Figure 11A:
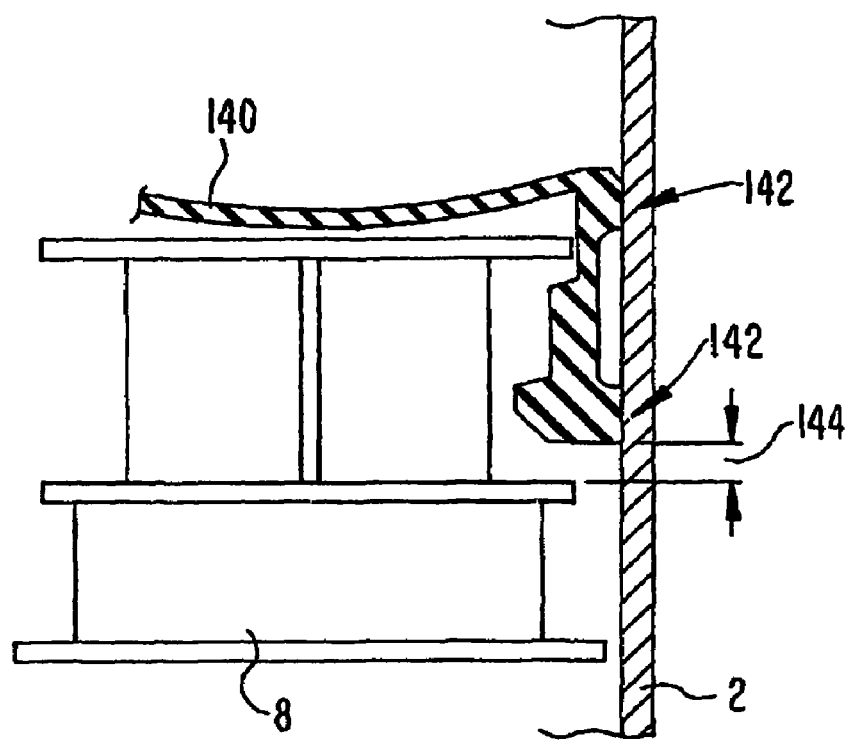
FIGS. 11a and 11b show vertical cross sections of a preferred seal for the plunger of a syringe.
Figure 11B:
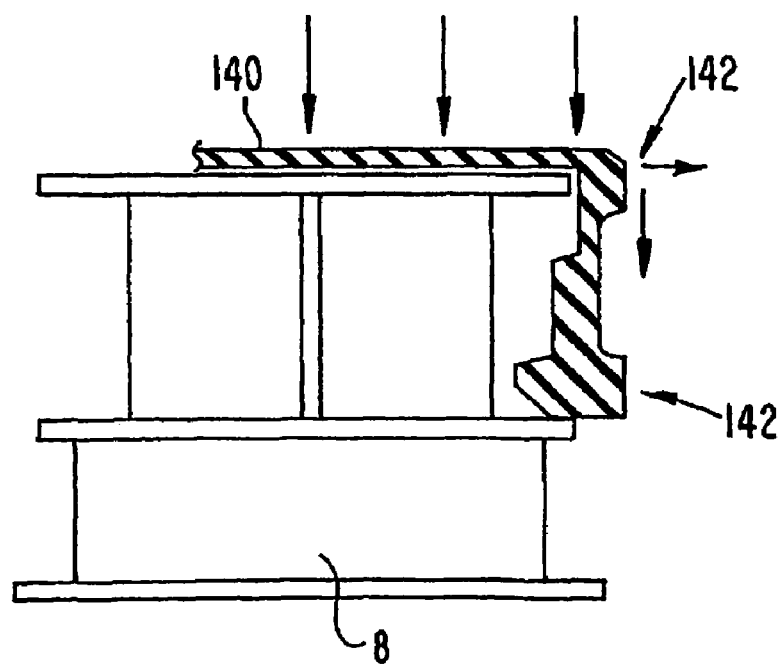

FIGS. 11a and 11b are vertical cross-sections of a preferred form of seal for the plunger seal 140. The seal is made of resilient material and engages the upper wall of the plunger. A vertical section extends over the edge of the upper wall and downwardly toward a lower wall. When the syringe is not undergoing centrifugation, the upper surface of the seal is generally concave upwardly, and edge portions 142 engage the interior surface of the syringe barrel 2. Also, the bottom of the seal is displaced from the lower wall by a gap 144. This provides an adequate seal to prevent leakage when the contents of the syringe are subjected to pressures near atmospheric. When the syringe is subjected to centrifugation, however, the pressure applied by the fluid on the seal 140 is greatly increased, and additional sealing capability is required. Thus, the seal 140 is designed to deform as shown in FIG. 11b by application of increased pressure by the fluids whereby the lower edge is made less concave, which presses the edge 142 outward against the wall 2 of the syringe with increased force increasing the sealing capability. The increase in the diameter of the seal due to its flattening out is accommodated by a reduction in the size of the gap 144.

Figure 12:
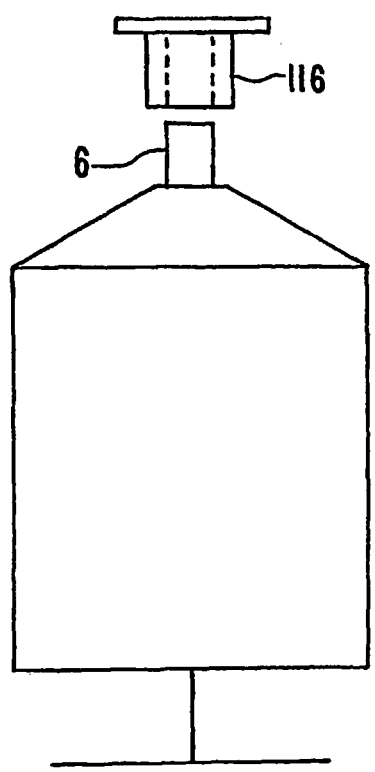
FIG. 12 illustrates a syringe according to the invention having a cap assembly that is attached during centrifugation.

FIG. 12 illustrates a further improvement. During centrifugation, the centrifugal forces on the fluids, the plunger, and the syringe barrel are strong enough that the plunger will naturally move outward slightly. That will cause some air to enter the barrel cavity. When the centrifugation terminates, the elements may recover their initial positions, which causes expression of the air. To allow this to occur without compromising sterility, a cap 116 of hydrophobic material is placed over the end of the tip 6 after blood has been drawn into the syringe. This provides a barrier to entry of bacteria after the blood has been drawn into the syringe and prevents discharge of blood from the syringe during handing and centrifugation.

Modifications within the scope of the appended claims will be apparent to those of skill in the art.

We claim:

1. A disk assembly for use in centrifugation comprising first and second elements arranged for relative movement and made of materials having respective densities such that said first element floats above said second element in a fluid, and said second element assumes a predetermined position in said fluid, and a pin extending from said first element and carrying said second element.

2. An assembly for use in centrifugal separation of a fluid into components, comprising a barrel configured to contain said fluid and having an end portion through which fluid components can be expressed from said barrel, and upper and lower elements arranged in said barrel for movement in said fluid, said upper and lower elements being made of materials with respective densities such that said upper element floats above said lower element in said fluid after centrifugation with said lower element floating in a predetermined position in said fluid with respect to a desired component of said fluid, and wherein the configuration of the interior surface of said end portion of said barrel conforms to the configuration of an upper surface of said upper element, whereby a component of said fluid above said upper element may be expressed, and said upper element has a fluid channel to pass fluid from beneath said upper element whereby a component of said fluid between said upper and lower elements may be subsequently expressed with said upper component in contact with said end portion.

3. An assembly according to claim 2 further including a pin extending from said first element and carrying said second element.

4. An assembly according to claim 3 further comprising a third element below said second element for providing stability to said assembly.

5. An assembly according to claim 2 wherein one of said elements is made of materials having a density gradient in a vertical direction.

6. An assembly according to claim 5 wherein said one of said elements is conical.

7. An assembly according to claim 2 further comprising a peripheral seal on at least one of said elements.

8. An assembly according to claim 2 wherein said barrel comprises a syringe.

9. A method of separating components of a fluid by centrifugation comprising the steps of providing a syringe having a barrel with an end portion and upper and lower spaced floating elements in said barrel, said upper and lower elements having respective densities such that said upper element floats above said lower element in said fluid after centrifugation with said lower element in a predetermined position in said fluid, and the configuration of an interior surface of said end portion conforms to the configuration of an upper surface of said upper element, drawing said fluid into said syringe, placing said syringe and fluid in a centrifuge and subjecting them to centrifugation, and expressing a first separated component above said upper element from said syringe through said end portion, and subsequently expressing a second separated component between said upper and lower elements from said end portion.

10. A method according to claim 9 wherein said step of expressing comprises expressing a first component until said upper surface of said upper element engages said interior surface.

11. A method according to claim 9 wherein said upper and lower elements are connected to each other to define their maximum separation.

12. A method according to claim 9 wherein said upper and lower elements are vertically movable with respect to each other.

13. A method according to claim 12 wherein said step of expressing comprises the step of causing said lower element to move toward said upper element.

14. A method according to claim 9 wherein said first and second elements are at a fixed distance from each other.

15. A method according to claim 14 wherein said step of expressing comprises causing a fluid component below said lower element to flow into a space between said upper and lower elements to expel a fluid component previously in said space.

16. An assembly according to claim 2 wherein said upper and lower elements are configured to provide a space between them and comprises means for allowing a fluid below said lower element to flow into said space and express fluids in said space through said fluid channel.

17. An assembly according to claim 16 wherein said means for allowing comprises spaced strips.

18. An assembly according to claim 2 wherein said upper and lower elements are movable with respect to each other and configured to provide a space between them for receiving a second component of said fluid and to express said second component of said fluid as said upper and lower elements move toward each other.

19. An assembly according to claim 18 wherein a periphery of said upper element slidingly engages a periphery of said lower element whereby said upper element may move with respect to said lower element.

20. An assembly according to claim 18 further comprising a pin on which one of said upper and lower elements moves when said upper element moves with respect to said lower element.

21. An assembly according to claim 18 wherein a lower surface of said upper element and an upper surface of said lower element have mating troughs.

22. A disk assembly according to claim 1 further comprising a third element below said second element for providing stability to said assembly.

23. A disk assembly according to claim 1 wherein said first element includes a fluid channel to pass fluid from beneath said upper element whereby a component of said fluid between said first and second elements can be expressed through said fluid channel.

* * * * *